United States Patent
Landgraf

(10) Patent No.: US 7,217,163 B2
(45) Date of Patent: May 15, 2007

(54) CONTACT CONNECTION ADAPTER FOR PRODUCING AN INTERMITTENT ELECTRICAL CONTACT BETWEEN TWO PLUGS

(75) Inventor: Tassilo Landgraf, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 0 days.

(21) Appl. No.: 11/409,266

(22) Filed: Apr. 24, 2006

(65) Prior Publication Data

US 2006/0240714 A1    Oct. 26, 2006

(30) Foreign Application Priority Data

Apr. 22, 2005    (DE) ..................... 10 2005 018 806

(51) Int. Cl.
  *H01R 9/22*    (2006.01)
(52) U.S. Cl. ..................... 439/909; 439/668; 439/948; 439/938; 607/37
(58) Field of Classification Search ............... 439/668, 439/669, 638, 639, 909, 948; 607/37
  See application file for complete search history.

(56) References Cited

U.S. PATENT DOCUMENTS

| | | | |
|---|---|---|---|
| 4,860,750 A * | 8/1989 | Frey et al. ..................... 607/37 |
| 5,413,595 A * | 5/1995 | Stutz, Jr. ..................... 607/37 |
| 5,782,892 A | 7/1998 | Castle et al. |
| 6,044,302 A * | 3/2000 | Persuitti et al. ............... 607/37 |
| 6,343,233 B1 | 1/2002 | Werner et al. |
| 7,047,077 B2 * | 5/2006 | Hansen et al. ................ 607/37 |
| 2003/0120327 A1 | 6/2003 | Tobritzhofer et al. |

FOREIGN PATENT DOCUMENTS

| | | |
|---|---|---|
| DE | G 88 08 698.4 U1 | 11/1988 |
| DE | 198 10 262 A1 | 9/1999 |
| DE | 199 38 960 A1 | 2/2001 |
| EP | 0 826 390 A2 | 3/1998 |

OTHER PUBLICATIONS

Disclosed Anonymously, "Cable connector for electrical measurements", *Research Disclosure, Mason Publications*, Hampshire, Great Britain, Bd. 395, Nr. 11, Mar. 1997, XP007121588, ISSN: 0374-4353.

* cited by examiner

*Primary Examiner*—Truc Nguyen
(74) *Attorney, Agent, or Firm*—Browdy and Neimark, PLLC

(57) ABSTRACT

A contact connection adapter for producing an intermittent electrical contact between two plugs has a main body and two socket-like receptacles placed thereon for the plugs. The cross-sections of the receptacle receiving the plugs to be connected intersect peripherally in this case in such a way that the plugs press against one another at their lateral contact faces and produce an electrical contact.

8 Claims, 2 Drawing Sheets

CONTACT CONNECTION ADAPTER FOR PRODUCING AN INTERMITTENT ELECTRICAL CONTACT BETWEEN TWO PLUGS

BACKGROUND OF THE INVENTION

1. Field of the Invention

The present invention relates to a contact connection adapter for producing an intermittent electrical contact between a first plug, particularly a standard terminal plug of a cardiac pacemaker electrode, and at least one second plug, particularly a typical laboratory plug for intermittent connection of the electrode to a stimulus threshold analyzer.

2. Background Art

The background of the present invention is the procedure during implantation of a cardiac pacemaker, defibrillator, or similar cardiological device, whose electrophysiological stimulation pulses are delivered by appropriate electrodes positioned in or on the heart. During the implantation procedure, the electrodes are typically advanced in a controlled way via the vascular system of the patient with the aid of a mandrel inserted into the electrode. This mandrel runs coaxially through the proximal terminal plug of the electrode. This plug is typically a plug standardized for medical application, designated IS-1/IS-4/DF-1, etc., for example, which may be implemented as unipolar or bipolar.

After an electrode is seated, its seat and stimulation pulse delivery behavior must be analyzed, for which a stimulus threshold analyzer is responsible. This device simulates the cardiac pacemaker otherwise coupled via the electrode terminal plug and must be electrically connected to the electrode plug for this purpose. However, this may not be performed by simply plugging the plug into the device, since the electrode plug must be kept sterile, and, in addition, the mandrel is not to be pulled out of the electrode yet for the present test, since repositioning of the electrode with the aid of the control mandrel may possibly be necessary. Since the mandrel end is guided through the plug, the plug may not be inserted into a device socket in any case.

DE 198 10 262 A1 (=U.S. Pat. No. 6,708,067 B1) discloses a test cable assembly, in which, on a cardboard-like support, a terminal pole of the electrode plug may be fixed on a clamp terminal attached to the support. The second pole, typically an electrode terminal ring, is contacted via an alligator clip, which simultaneously produces a further mechanical connection between the paperboard-like support and the electrode plug. Clamp terminal and alligator clip are electrically connected via thin litz wires, which may be plugged into a fitting socket of the test unit via a corresponding plug device.

This previously known achievement of the object has a provisional character, and, in addition, multiple steps are necessary for the production of the adapter, namely cutting the paperboard support to length and wiring and attaching the terminal clamp and alligator clip. Handling this test adapter is cumbersome and the contact provided, particularly to the alligator clip, is in need of improvement in its reliability.

SUMMARY OF THE INVENTION

The present invention is based on the object of specifying a contact connection adapter of the type cited at the beginning, which may be manufactured with significantly less production complexity, is extremely simple to handle, and offers high contact reliability between the electrical parts to be connected at the same time.

This object is achieved by a contact connection adapter comprising a main body, in which socket-like receptacles for the two plugs to be connected, in the concrete example the terminal plug of a cardiac pacemaker electrode and a typical laboratory plug on a laboratory cable leading to the stimulus threshold analyzer, are placed. The cross-sections of these receptacles intersect peripherally in such a way that the plugs plugged into the receptacles press against one another at their lateral contact faces and produce an electrical contact.

It may be seen that the main body itself does not require any contact elements to produce an electrical contact. This is produced solely via the plugged-in plugs directly with one another. Therefore, the contact connection adapter may be produced from a uniform material, such as plastic which may be injection molded. The adapter is thus also distinguished by especially good ability to be sterilized.

Preferred embodiments of the contact connection adapter and features, details, and advantages thereof will become clear from the following description of the present invention on the basis of the attached drawing.

DESCRIPTION OF THE PREFERRED EMBODIMENTS

Figure 1:
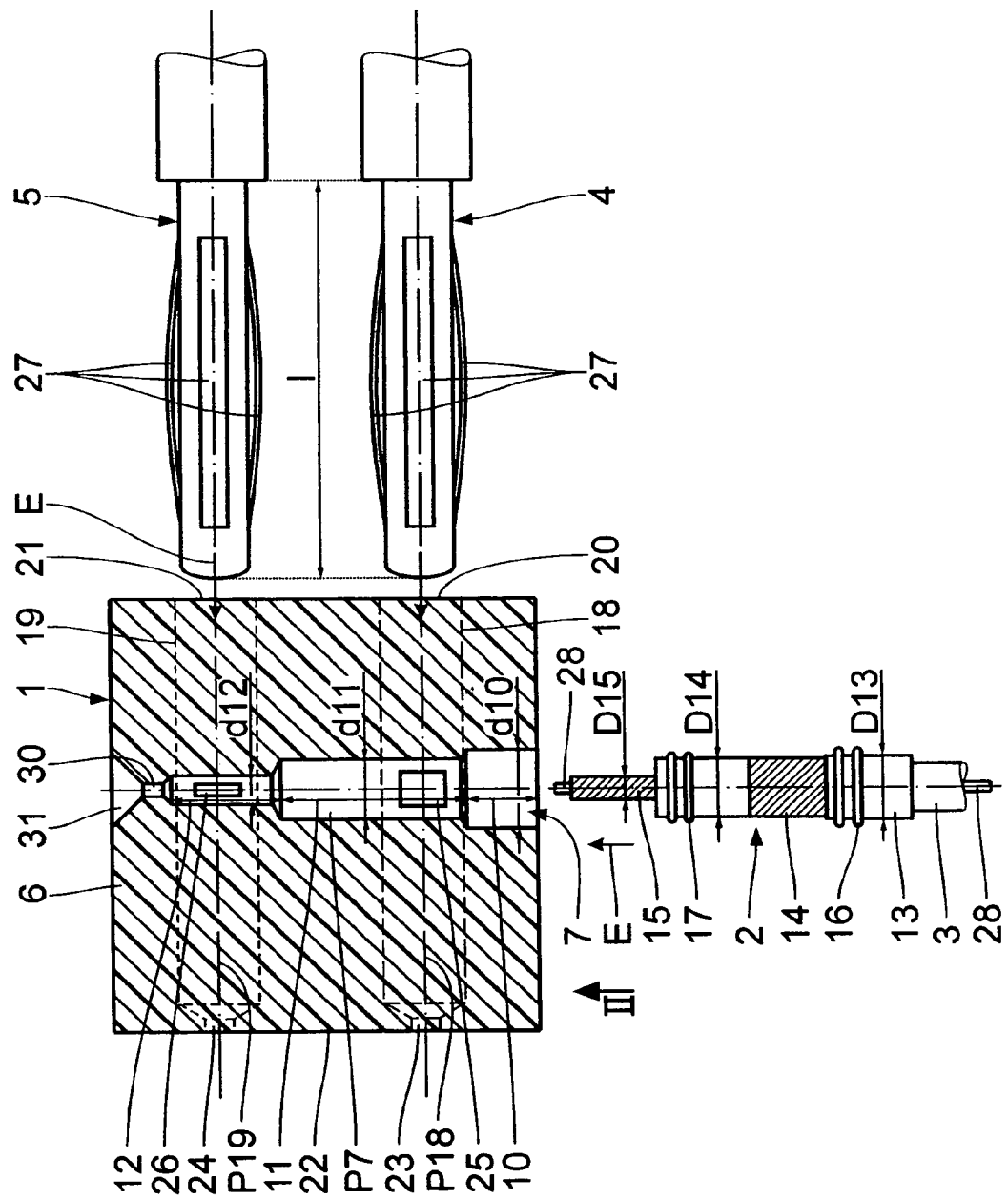
FIG. 1 shows a horizontal section of a contact connection adapter along section line I–I in FIG. 2 having plugs to be connected before they are inserted into the adapter.
Figure 2:
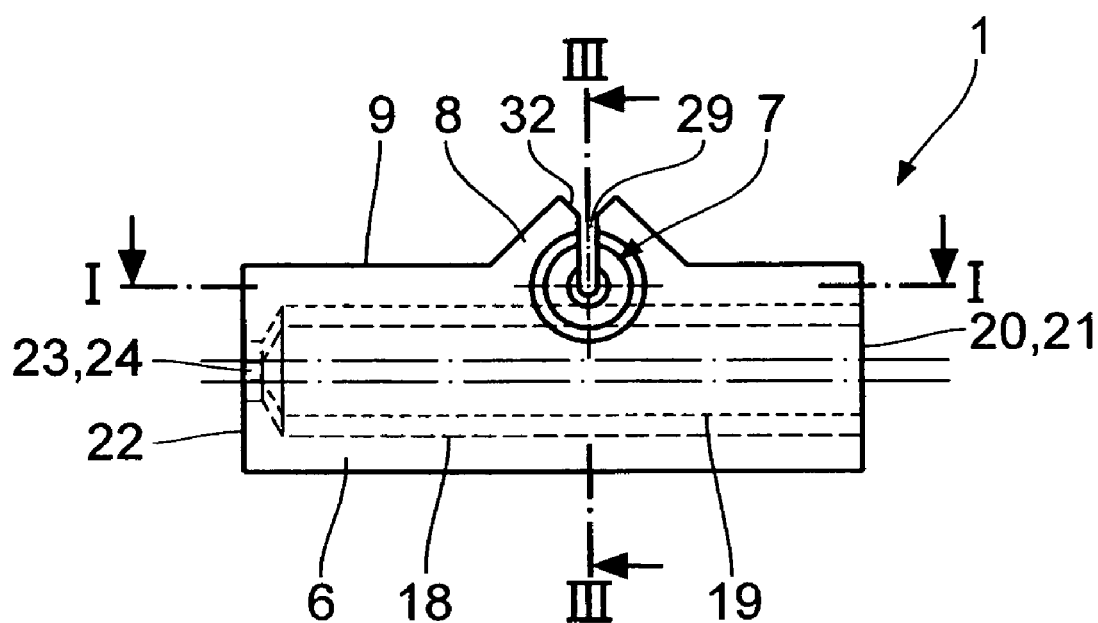
FIG. 2 shows a side view of the adapter from arrow direction II in FIG. 1.

The contact connection adapter 1 shown in the drawing is used for producing an intermittent electrical contact between a standardized IS-1/IS-4/DF-1 terminal plug 2 of a cardiac electrode 3 shown cut away in FIG. 1 and, in addition, two typical laboratory plugs 4, 5—colloquially referred to as "banana plugs"—which are to be electrically connected via appropriate cables to the terminal sockets of a stimulus threshold analyzer (not shown in greater detail).

The adapter 1 has an essentially cuboid main body 6, which is injection molded from a transparent, sterilizable plastic material in one piece. A socket-like receptacle 7 is placed in the main body approximately centrally, but shifted toward the top and running parallel thereto, whose cross-sectional area pointing to the outside is housed in a projection 8, which is triangular in profile. This extends beyond the top 9 of the adapter 1.

As may be seen from FIG. 1, the receptacle 7 is stepped twice starting from a plug area at the mouth having a diameter d10, namely to a somewhat narrower plug area 11 having the diameter d11 and a deepest plug area 12 having an even smaller diameter d12. The plug areas 10, 11, and 12 have their diameters d10, d11, and d12 tailored to the corresponding external diameters D13, D14, D15 of the plug shaft 13, the annular contact 14, and the tip contact 15 placed at the tip of the plug 2. The shaft 13 is separated from annular contact 14 by a double peripheral annular seal 16 in this case. Likewise, a further pair of annular seals 17 are provided on the shaft area following the annular contact 14 before the step to the tip contact 15.

To receive the two laboratory plugs 4, 5, the adapter has an essentially cylindrical receptacle 18, 19 in each of two planes P18 and P19, which lie one behind another in the insertion direction E and are perpendicular thereto. As may be seen from FIG. 1, the depth of these receptacles 18, 19 approximately corresponds to the length l of the laboratory plugs 4, 5 and the receptacles end shortly before the narrow side 22 of the adapter 1 facing away from the mouth 20, 21. They are each permeable to sterilization liquid there via an opening 23, 24.

Figure 3:
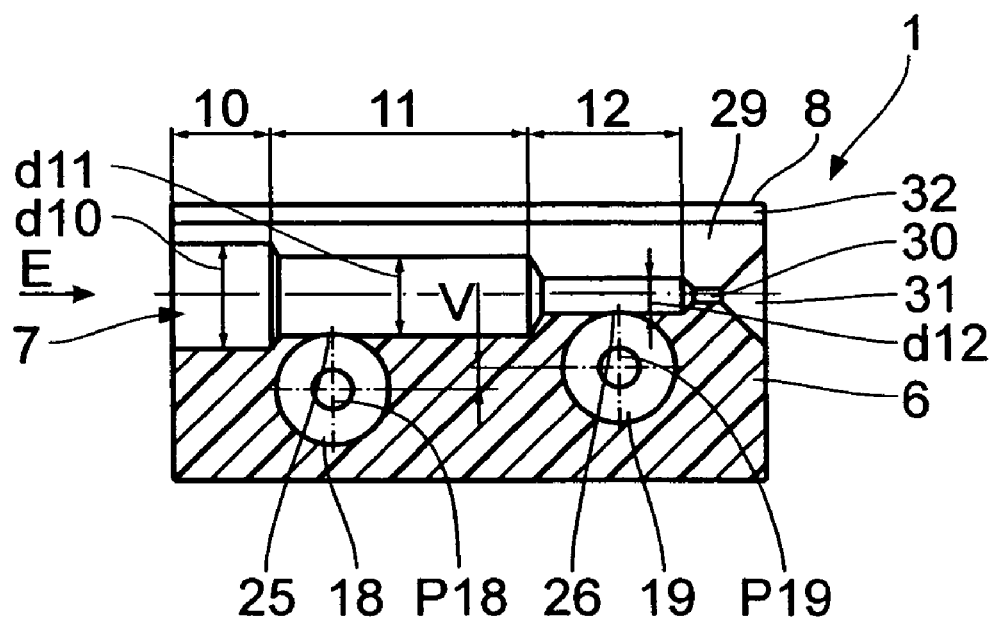
FIG. 3 shows a section of the adapter along section line III–III in FIG. 2.

As may be seen from FIG. 3 in particular, the cross-sections of the receptacle 7 for the IS-1/IS-4/DF-1 plug 2 and the two receptacles for the laboratory plugs 4, 5 intersect slightly peripherally, so that the two cross-sectional volumes pass into one another via contact windows 25, 26 (FIG. 1). If the IS-1 plug 2 is plugged into the receptacle 7 and a laboratory plug 4, 5 is plugged into each of the receptacles 18, 19, the spring lamellae 27 of the laboratory plugs 4, 5 provide an optimum electrical connection to the annular contact 14 or tip contact 15 of the plug 2 via the contact windows 25, 26.

As may be seen from FIG. 3 in particular, the two receptacles 18, 19 have an offset V to one another for adaptation to the stepped diameter reduction of the receptacle 7.

For the above-mentioned mandrel seated in the electrode, which is merely partially indicated in FIG. 1 at reference number 28, the receptacle 7 for the plug 2 is open laterally over its complete length through a passage slot 29 provided in the projection 8. Furthermore, its innermost plug area 12 continues in the coaxial direction in a passage hole 30, which expands into a funnel-shaped mouth 31. Via the passage slot 29 and a passage hole 30, the section of the mandrel 28 running in front of the tip contact 15 may be inserted into the receptacle 7 from the side. Direct threading is not possible, since the mandrel ends in a voluminous control handle. After the insertion of the mandrel into the receptacle 7, the plug 2 may be plugged in. To make inserting the mandrel easier, the passage slot 29 is provided with insertion bevels 32.

What is claimed is:

1. A contact connection adapter for producing an intermittent electrical contact between a first plug (2), particularly a standard terminal plug of a cardiac pacemaker electrode (3), and at least one further plug (4, 5), particularly a typical laboratory plug of a laboratory cable for intermittent connection of the electrode (3) to a stimulus threshold analyzer, comprising
   a main body (6),
   a first socket-like receptacle (7), which is placed in the main body (6), for the first plug (2), and
   at least one second socket-like receptacle (18, 19), which is placed in the main body (6), for the at least one further plug (4, 5), the cross-sections of the first and the at least one second receptacles (7, 18, 19) intersecting peripherally in such a way that plugs (2, 4, 5) plugged into the receptacles (7, 18, 19) press against one another at their lateral contact faces (14, 15, 27) and produce an electrical contact.

2. The contact connection adapter according to claim 1, wherein the receptacles (7, 18, 19) for the plugs (2, 4, 5) are situated having their longitudinal axes in planes (P7, P18, P19) intersecting one another perpendicularly.

3. The contact connection adapter according to claim 1, wherein, for a bipolar or unipolar plug (2), a receptacle (7), whose diameter (d11, d12) is stepped twice with increasing socket depth, is provided for its adaptation to diameters (D13, D14, D15), which are reduced in steps, of plug shaft (13), annular contact (14), and tip contact (15) of the plug (2).

4. The contact connection adapter according to claim 1, wherein the first socket-like receptacle (7) for the first plug (2) is open both at a deep end in a longitudinal axial direction via a thin passage (30) and also along its entire depth via a lateral, longitudinally parallel passage slot (29).

5. The contact connection adapter according to claim 1, wherein the at 20 least one second receptacle (18, 19) for the at least one further plug (4, 5) has an opening at a deep end (23, 24).

6. The contact connection adapter according to claim 1, wherein the main body (6) comprises a transparent, sterilizable plastic material.

7. The contact connection adapter according to claim 3, wherein two receptacles (18, 19), which lie parallel next one another, for two further plugs (4, 5) are placed in the main body (6), which have an offset (V) to one another corresponding to a diameter reduction between annular contact (14) and tip contact (15) of the bipolar plug (2).

8. The contact connection adapter according to claim 4, wherein the passage slot (29) is provided with insertion bevels (32).

* * * * *